(12) United States Patent
Kozin et al.

(10) Patent No.: US 6,665,948 B1
(45) Date of Patent: Dec. 23, 2003

(54) DRILL BIT PENETRATION MEASUREMENT SYSTEM AND METHOD

(76) Inventors: Scott Hal Kozin, 180 Berwind Cir., Radnor, PA (US) 19087; Joseph C. McGinley, 6100 Henry Ave. #2A, Philadelphia, PA (US) 19128; Scott T. Porter, 2610 Pine St., Philadelphia, PA (US) 19103

( * ) Notice: Subject to any disclaimer, the term of this patent is extended or adjusted under 35 U.S.C. 154(b) by 0 days.

(21) Appl. No.: 10/235,106

(22) Filed: Sep. 5, 2002

(51) Int. Cl.$^7$ ................................................ B23B 49/00
(52) U.S. Cl. ........................... 33/833; 33/638; 175/45; 433/27; 408/8; 408/16
(58) Field of Search .................... 33/833, 512, 542, 33/832, 836, 638; 175/40, 45; 433/27; 408/8, 10, 12, 13, 16

(56) References Cited

U.S. PATENT DOCUMENTS

| | | | |
|---|---|---|---|
| 4,014,621 A | * 3/1977 | Johnson et al. | 33/833 |
| 4,310,269 A | * 1/1982 | Neu et al. | 408/8 |
| 4,329,095 A | * 5/1982 | Schmuck | 408/16 |
| 4,710,075 A | * 12/1987 | Davison | 33/512 |
| 4,723,911 A | 2/1988 | Kurtz | 433/27 |
| 4,765,333 A | 8/1988 | Bray | |
| 4,867,158 A | 9/1989 | Sugg | |
| 4,951,690 A | 8/1990 | Baker | |
| 5,022,798 A | 6/1991 | Eckman | 408/12 |
| 5,361,504 A | * 11/1994 | Huang | 33/371 |
| 5,380,333 A | 1/1995 | Meloul et al. | |
| 5,411,503 A | 5/1995 | Hollstien et al. | |
| 5,584,838 A | 12/1996 | Rona et al. | |

* cited by examiner

*Primary Examiner*—Christopher W. Fulton
(74) *Attorney, Agent, or Firm*—Akin Gump Strauss Hauer & Feld, L.L.P.

(57) ABSTRACT

A drill bit penetration measurement system and method for determining a depth of penetration of a rotating drill bit in a bore. A first sensor outputs a first signal representative of a displacement of the leading edge of the drill bit in the bore. A second sensor outputs a second signal representative of a force applied to the leading edge of the drill bit. A processor outputs a third signal representative of the depth of penetration of the leading edge of the drill bit when the leading edge of the drill bit passes from a first medium having a first density to a second medium having a second density. The third signal is based on the first and second signals.

16 Claims, 9 Drawing Sheets

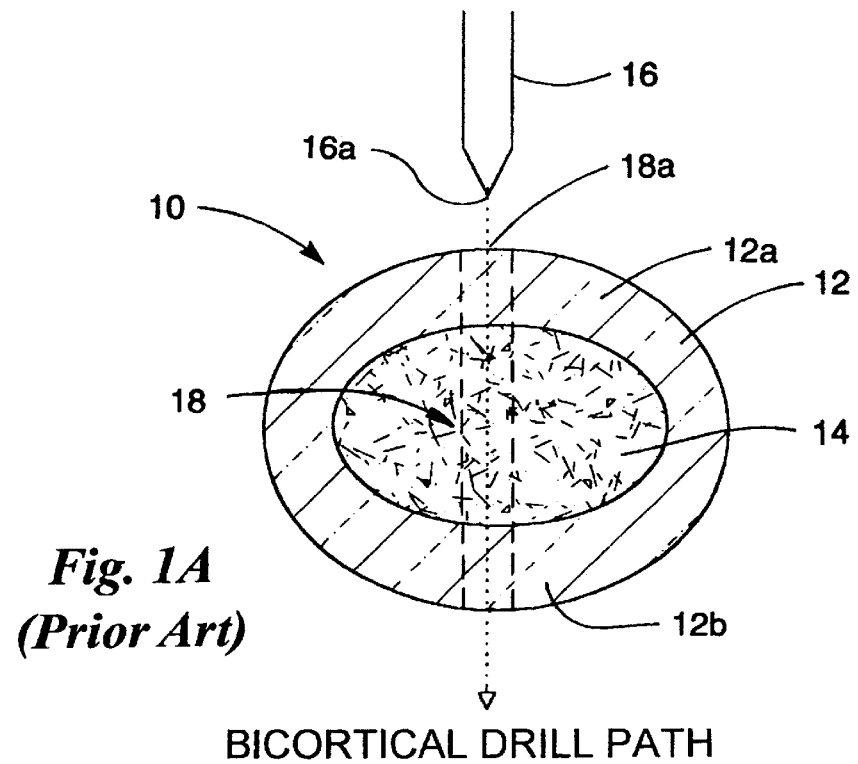
Fig. 1A (Prior Art) BICORTICAL DRILL PATH
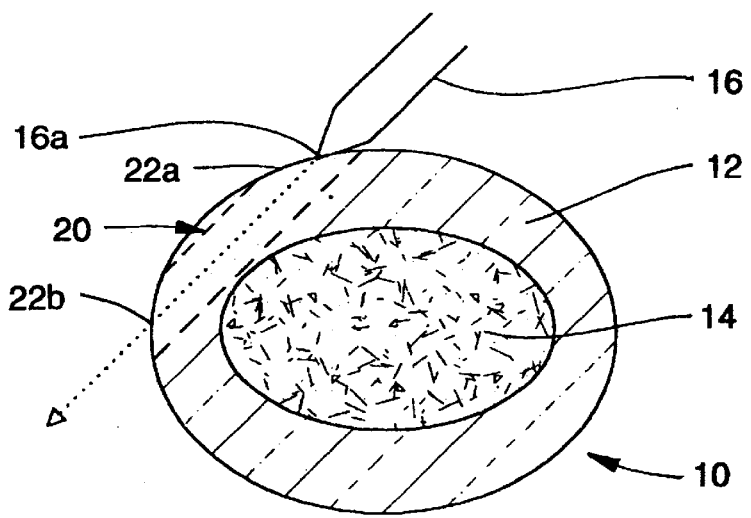
Fig. 1B (Prior Art) UNICORTICAL DRILL PATH

DRILL BIT PENETRATION MEASUREMENT SYSTEM AND METHOD

BACKGROUND OF THE INVENTION

The present invention relates generally to a system and method for determining, with respect to a reference point, a depth of penetration of a leading edge of a rotating drill bit in a bore when the leading edge of the drill bit passes from a first medium having a first density to a second medium having a second density. More specifically, the present invention relates to a system and method for determining the length of either a unicortical or bicortical bore without removing the drill bit from the bore.

Inadequate and inaccurate depth measurement following orthopedic drilling procedures results in incorrect screw lengths which can lead to surgical complications. Furthermore, determining the correct screw length can be a time consuming procedure which is undesirable when tissue is exposed and subject to infection.

As shown in FIGS. 1A and 1B, the bony structure of the human anatomy consists mainly of cortical bone 10 having a hard outer cortex 12 and a soft inner medullary layer 14. Following traumatic injury, plate and screw placement is critical for adequate repair. Improper drilling lengths could lead to device instability, damage to anatomic structures, or device failure.

As shown in FIG. 1A, when using a rotating drill bit 16 to form a bicortical bore 18 through the cortical bone 10, the rotating drill bit 16 passes through a first portion 12a of the hard outer cortex 12, a soft non-resistant medullary layer 14, and a second portion 12b of the hard outer cortex 12.

As shown in FIG. 1B, when using a rotating drill bit 16 to form a unicortical bore 20 through the cortical bone 10, the rotating drill bit 16 passes through an entry point 22a of the hard outer cortex 12 and an exit point 22b of the hard outer cortex 12 without penetrating the soft non-resistant medullary layer 14.

Current techniques for drilling and screw placement are two-step processes at best. During an operation, a bore is first drilled by a surgeon until the surgeon "feels" the drill bit pass completely through the bony structure. A depth gage (not shown) is then inserted into the bore, grasped against the proximal end and a depth is recorded. A possible resulting complication of this procedure is that the surgeon may not precisely "feel" the drill bit pass through the second cortical layer, thereby possibly damaging tissue on the opposite side of the bone. Another complication may occur if the depth gage is not properly inserted into the hole. If the gage is grasped prior to passing the distal end of the bore, a size will be determined that is smaller than the true depth.

The process of drilling and depth measurement often requires more than one attempt. Conservative drilling may result in incomplete drilling requiring multiple passes. Furthermore, multiple depth measurements may be obtained to confirm accurate placement of the gage. This process consumes a substantial amount of surgical time resulting in a large cost per patient. By combining the drilling and depth measurement process into one accurate procedure, cost is reduced along with a decrease in patient morbidity. What is needed is a simpler, cheaper, safer, faster and more accurate method and apparatus for measuring the depth of drill bit penetration and determining spatial location in a material having a varying density, such as cortical bone.

BRIEF SUMMARY OF THE INVENTION

One aspect of the present invention is a drill bit penetration measurement system for determining, with respect to a reference point, a depth of penetration of a leading edge of a rotating drill bit in a bore when the leading edge of the drill bit passes from a first medium to a second medium. The first medium is contiguous with the second medium. The first medium has a first density. The second medium has a second density. The system comprising a first sensor, a second sensor, and a processor. The first sensor outputs a first signal representative of a displacement, with respect to the reference point, of the leading edge of the drill bit in the bore. The second sensor outputs a second signal representative of a force applied to the leading edge of the drill bit. The processor is in electrical communication with the first and second sensors. The processor is configured in a first mode to output a third signal representative of the depth of penetration of the leading edge of the drill bit when the leading edge of the drill bit passes from the first medium to the second medium. The third signal is based on the first and second signals.

Another aspect of the present invention is a drill bit penetration measurement system for determining, with respect to a reference point, a depth of penetration of a leading edge of a rotating drill bit in a bore when the leading edge of the drill bit passes from a first medium to a second medium. The first medium has a first density. The second medium has a second density. The drill bit is rotatably driven by a drive within a drill housing. The system comprises a drill bit displacement measurement assembly, a drill bit load measurement assembly and a controller assembly. The drill bit displacement measurement assembly is connected to the drill housing. The displacement measurement assembly has a first sensor outputting a first signal representative of a displacement of the leading edge of the drill bit in the bore. The drill bit load measurement assembly comprises a housing, a thrust assembly about which the housing is rotatable, a drill chuck and a second sensor. The housing has an axis of rotation. The housing is removably connected to the drive for rotation thereby. The drill chuck is connected to the housing for rotation therewith and to the thrust assembly for rotation with respect thereto. The drill chuck is movable in translation along the axis of rotation of the housing. The second sensor is connected to the thrust assembly. The second sensor outputs a second signal representative of a force applied to the drill bit. The control assembly is in electrical communication with the first sensor and the second sensor. The control assembly has a processor configured in a first mode to output a third signal representative of the depth of penetration of the leading edge of the drill bit when the leading edge of the drill bit passes from the first medium to the second medium. The third signal is based on the first and second signals.

Still another aspect of the present invention is a method for determining, with respect to a reference point, a depth of penetration of a leading edge of a rotating drill bit in a bore when the leading edge of the drill bit transitions from a first medium to a second medium. The first medium is adjacent the second medium. The first medium has a first density. The second medium has a second density. The method comprises: establishing as the reference point an initial position of the leading edge of the drill bit; outputting a first signal representing the depth of penetration of the leading edge of the rotating drill bit in the bore; outputting a second signal representing a force applied to the leading edge of the drill bit; and outputting a third signal representative of the depth of penetration of the leading edge of the drill bit when the leading edge of the drill bit passes from the first medium to the second medium. The third signal is based on the first and second signals.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A is a sectional view of a bone illustrating a prior art method of using a drill mechanism to create a bicortical path through a cortical bone having multiple layers;

FIG. 1B is a sectional view of a bone illustrating a prior art method of using a drill mechanism to create a unicortical drill path through the outer layer of a cortical bone;

DETAILED DESCRIPTION OF THE INVENTION

Figure 2:
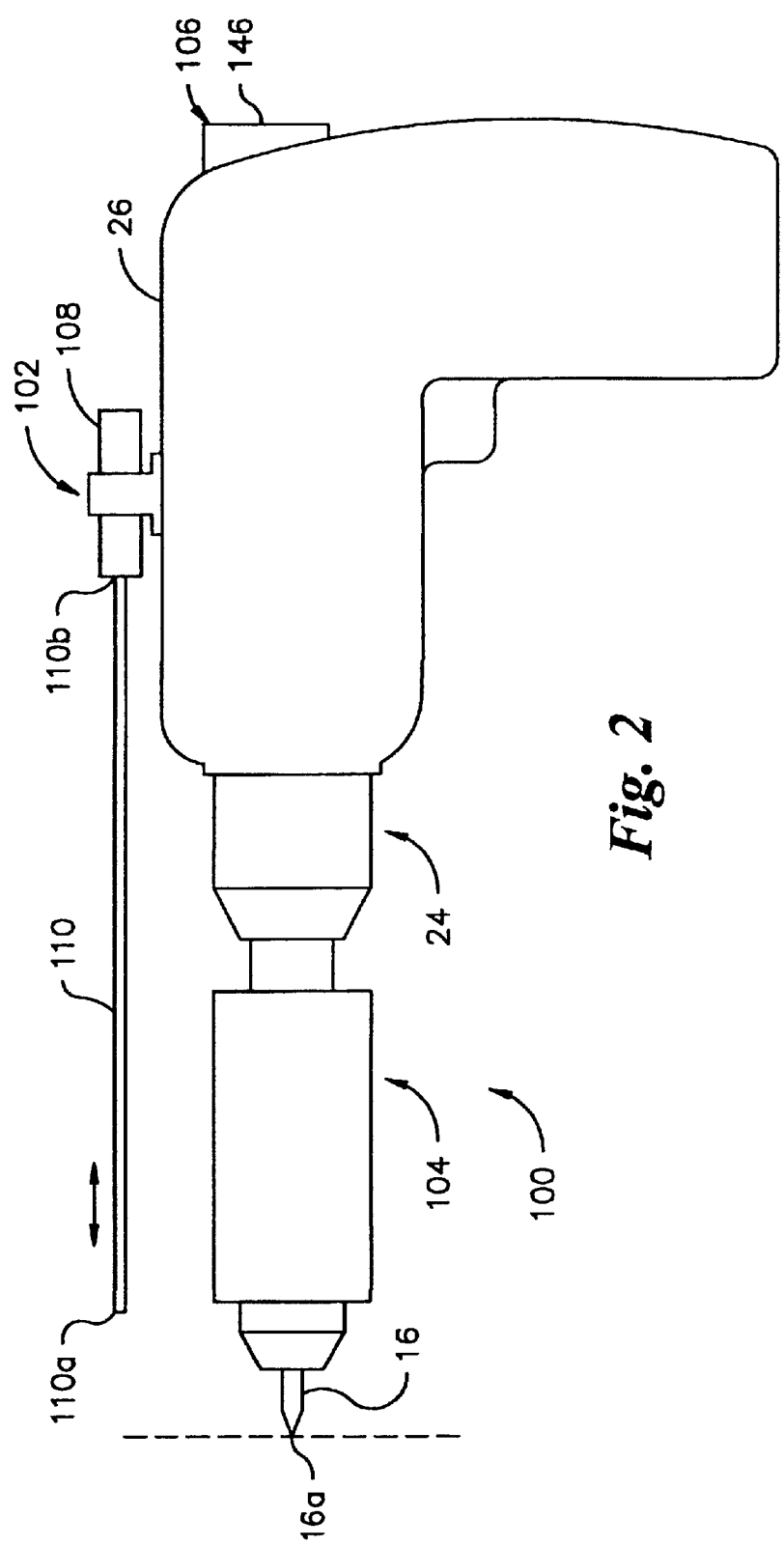
FIG. 2 is an elevation view, partially in cross section of a preferred embodiment of a real-time, drill bit penetration measurement system in accordance with the present invention.

Certain terminology is used in the following description for convenience only and is not limiting. The words "right," "left", "lower" and "upper" designate directions in the drawings to which reference is made. The words "inwardly" and "outwardly" refer to directions toward and away from, respectively, the geometric center of the drill bit penetration measurement system and designated parts thereof. The terminology includes the words above specifically mentioned, derivatives thereof and words of similar import.

Additionally, as used in the claims and in the corresponding portion of the specification, the word "a" means "at least one". Further, unless otherwise defined the word "about" when used in conjunction with a numerical value means a range of values corresponding to the numerical value plus or minus ten percent of the numerical value. Still further, the word "or" has the meaning of a Boolean inclusive "Or". For example, the phrase "A or B" means "A" alone or "B" alone or both "A" and "B".

Referring to the drawings in detail, where like numerals indicate like elements throughout there is shown in FIGS. 2–8 a first preferred embodiment of the drill bit penetration measurement system generally designated 100, and hereinafter referred to as the "Measurement System" 100, in accordance with the present invention. The Measurement System 100 is for determining, with respect to a reference point (not shown), a depth of penetration of the leading edge 16a of a rotating drill bit 16 in a bore when the leading edge 16a of the drill bit 16 passes from a first medium having a first density to a second medium adjacent the first medium and having a second density. The drill bit 16 is rotatably driven by a drive 24 in a drill housing 26 of any typical well known surgical drill. Preferably the first and second media are the hard outer cortex 12 and a medium such as air or other anatomical structure (not shown) surrounding the outer surface of the cortical bone 10 and the bore is either the bicortical bore 18 or the unicortical bore 20 being drilled in the cortical bone 10. (See FIGS. 1A–1B). However, those skilled in the art will understand from the present disclosure that the first and second media can be the hard outer cortex 12 and the soft inner medullary layer 14 of the cortical bone 10 or any adjacent media of different density without departing from the scope of the invention. The artisan will also understand that the reference point is a fixed point relative to which the displacement of the leading edge 16a of the drill bit 16 is measured and corresponds to an initial position of the Measurement System 100 as further discussed below.

Referring to FIGS. 2, 7A, 7B and 7C, the Measurement System 100 comprises a drill bit displacement measurement assembly 102, a drill bit load measurement assembly 104, and a controller assembly 106. The displacement measurement assembly 102 is connected to the drill housing 26. The connection can be made by a variety of well known mounting methods such as a mount that clamps to the displacement measurement assembly 102 and is attached to the drill housing 26 by one or more threaded fasteners. Alternative methods such as welding or adhesive bonding could also be used. The displacement measurement assembly 102 has a first sensor 108 that outputs a first signal 108s representative of a displacement, with respect to the reference point, of the leading edge 16a of the drill bit 16 in the bore being drilled. The displacement measurement assembly 102 preferably has an extension 110 that is displaceable along a longitudinal axis. The extension 110 has a distal end 110a that can be placed in registry with the reference point when the leading edge 16a of the drill bit 16 is positioned at the entry point, such as the entry point 18a of the bicortical bore 18 or the entry point 22a of the unicortical bore 20 shown in FIGS. 1a–1b and maintained in registry with the reference point throughout the drilling process. The reference point can be any anatomical structure proximal to the desired location of the bore to be drilled. The extension 110 has a proximal end 110b that is attached to the first sensor 102. Preferably the sensor 102 is a linear variable differential displacement transducer ("LVDT").

Figures 3A, 3B:
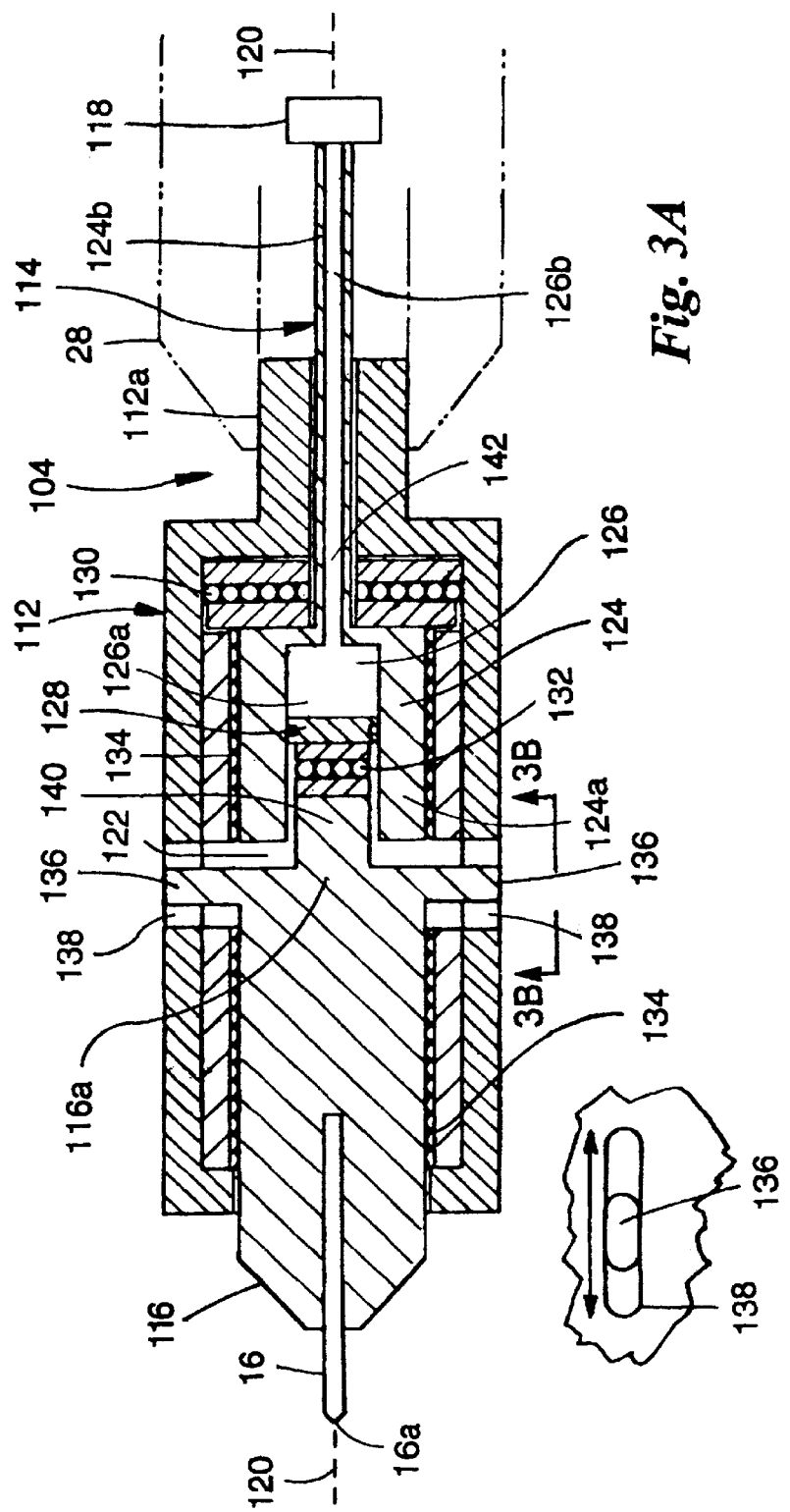
FIG. 3A is an enlarged sectional view of a first preferred embodiment of the drill bit load measurement assembly of FIG. 2.
FIG. 3B is a sectional view of a portion of the drill bit load measurement assembly taken along the line 3B—3B of FIG. 3A.

Referring to FIGS. 3A and 3B, the drill bit load measurement assembly 104 comprises a housing 112, a thrust assembly 114 about which the housing 112 is rotatable, a drill chuck 116 and a second sensor 118. The housing 112 has an axis of rotation 120 and is removably connected to the drive 24 for rotation thereby. Preferably, the housing 112 has a generally cylindrical-like shape and has a chamber 122 extending the length thereof for containing a portion of the thrust assembly 114 and a portion of the drill chuck 116. Preferably, but not necessarily, the housing 112 also has a proximal end 112a with an outer diameter sized for being secured in a drive chuck 28 of the drive 24. Those skilled in the art will understand from this disclosure that the drive chuck 28 can be any well known surgical drill chuck through which surgical instruments are insertable.

The thrust assembly 114 is preferably a tube 124 with a bore 126 therethrough. The bore 126 has a piston 128 moveable therein. The tube 124 has a first portion 124a having a first outer diameter and a second portion 124b having a second outer diameter less than the first outer diameter. Similarly, the bore 126 has a first portion 126a having a first inner diameter and a second portion 126b having a second inner diameter less than the first inner diameter. Preferably, the piston 128 is in the first portion 126a of the bore 126. The second portion 124b of the tube 114 extends beyond the proximal end 112a of the housing 112. The thrust assembly 114 is connected to the housing 112 by a first bearing 130 and to the drill chuck 116 by a second bearing 132, preferably connected to the piston 128. Preferably, the first and second bearings 130, 132 are thrust bearings suitable for use in a surgical environment. Alternatively, the first and second bearings 130, 132 could be any device that permits the housing 112 and the drill chuck 116 to rotate with respect to the thrust assembly 114 and allows a force applied to the leading edge 16a of the drill bit 16 to be transferred to the thrust assembly 114. Preferably, but not necessarily, the thrust assembly 114 also is journaled with the housing 112 by a third bearing 134.

The drill chuck 116 is connected to the housing 112 for rotation therewith and to the thrust assembly 114 for rotation with respect thereto. The drill chuck 116 is moveable in translation along the axis of rotation 120 of the housing 112. Preferably, the drill chuck 116 is a conventional surgical drill chuck having a proximal end 116a within the chamber 122 of the housing 112. The drill chuck is connected to the housing 112 by a tab 136 extending radially outwardly from the proximal end 116a of the drill chuck 116. The tab 136 extends into a corresponding slot 138 in the housing and is moveable therein in translation along the axis of rotation 120 of the housing 112. Preferably, but not necessarily, the drill chuck 116 has diametrically opposed tabs 136. Those of ordinary skill in the art will understand from the present disclosure that tabs 136 can be removably attached to the drill chuck 116 by a threaded fastener (not shown) to facilitate insertion of the proximal end 116a of the drill chuck into the housing 112. The proximal end 116a of the drill chuck 116 additionally has a projection 140 that extends into the bore 126 of the thrust assembly 114 and is connected by the second bearing 132 to the piston of the thrust assembly 114.

Figures 4A, 4B:
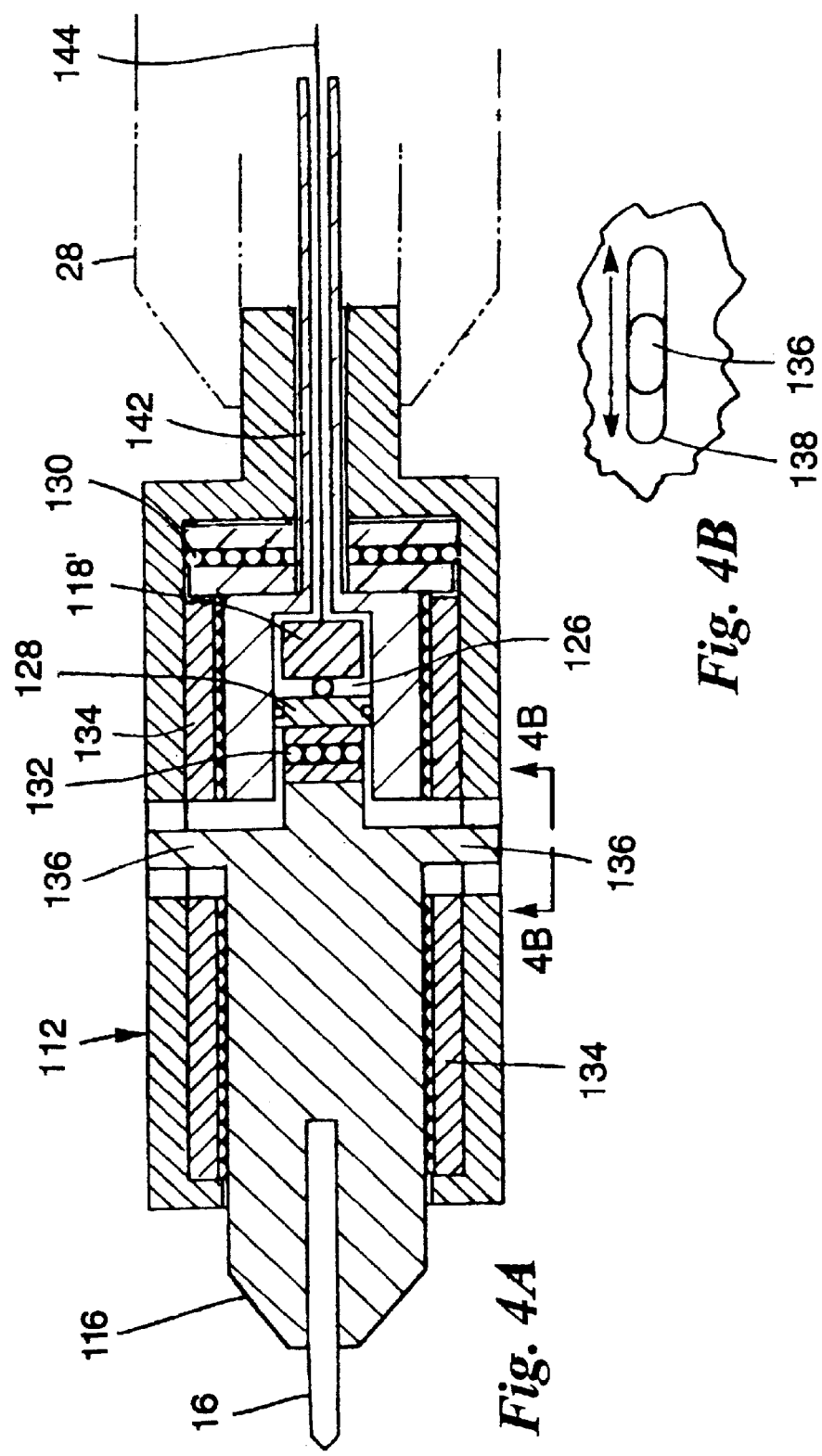
FIG. 4A is an enlarged sectional view of a second preferred embodiment of the drill bit load measurement assembly of FIG. 2.
FIG. 4B is a sectional view of a portion of the drill bit load measurement assembly taken along the line 4B—4B of FIG. 4A.

The second sensor 118 in connected to the thrust assembly 114 and outputs a second signal 118s representative of a force applied to the leading edge 16a of the drill bit 16. As shown in FIG. 3A, in one preferred embodiment of the present invention, the second sensor 118 is a hydraulic pressure transducer and a portion of the bore 126 forms a hydraulic chamber 142 connecting the second sensor 118 with the piston 128. As shown in FIG. 4A, in another preferred embodiment of the present invention, the second sensor 118' is a load cell, such as a piezo-electric device, adjacent the piston 128 and a portion of the bore 126 forms a conduit 142' through which passes an electrical conductor 144 connecting the piezo-electric device to the controller assembly 106.

Figure 5:
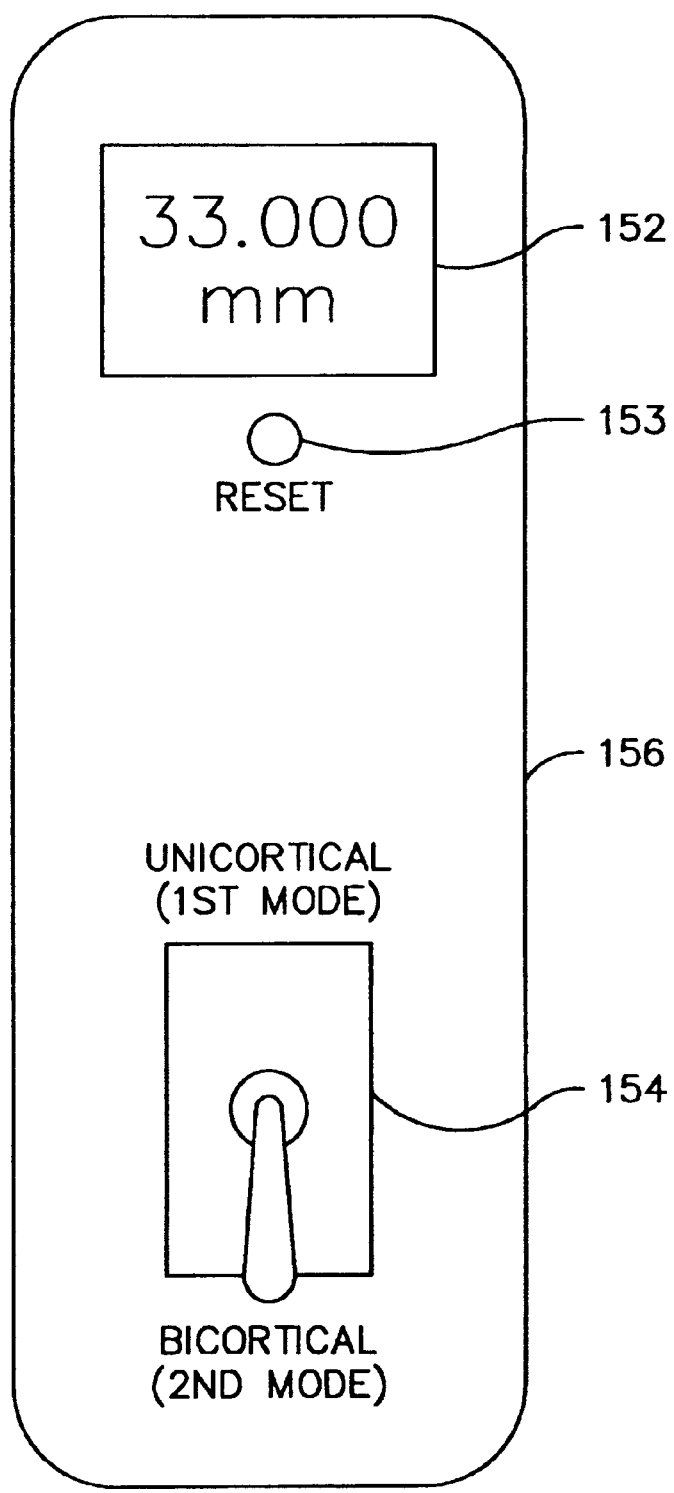
FIG. 5 is an elevation view of the control panel of the controller assembly of FIG. 2.
Figure 6:
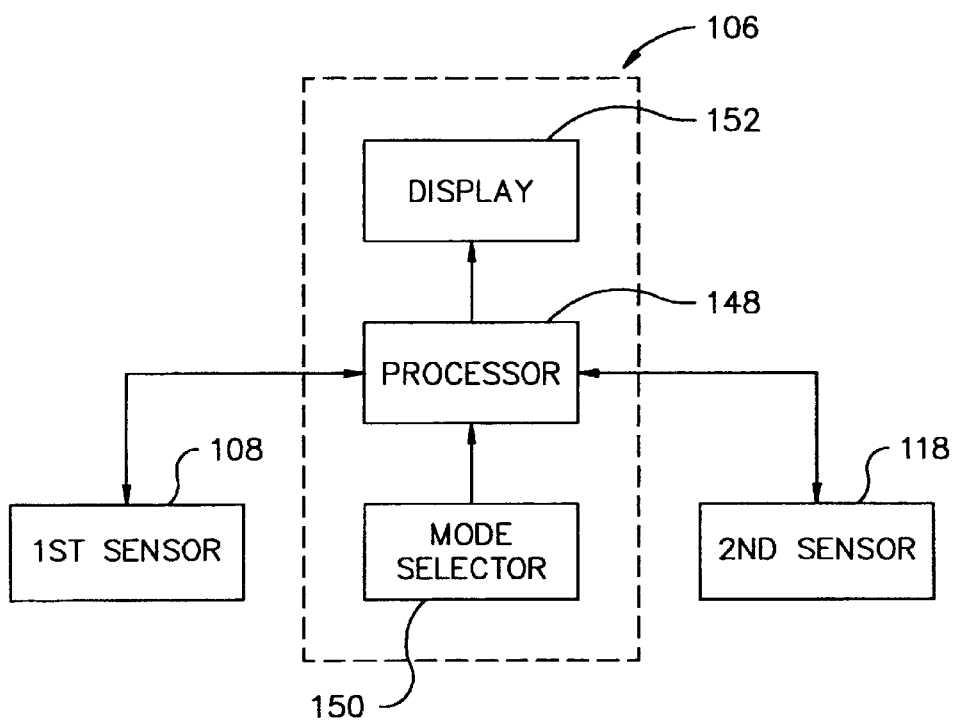
FIG. 6 is a schematic block diagram of the controller assembly of FIG. 2 and the inputs and outputs of the controller assembly.
Figures 7A, 7B, 7C:
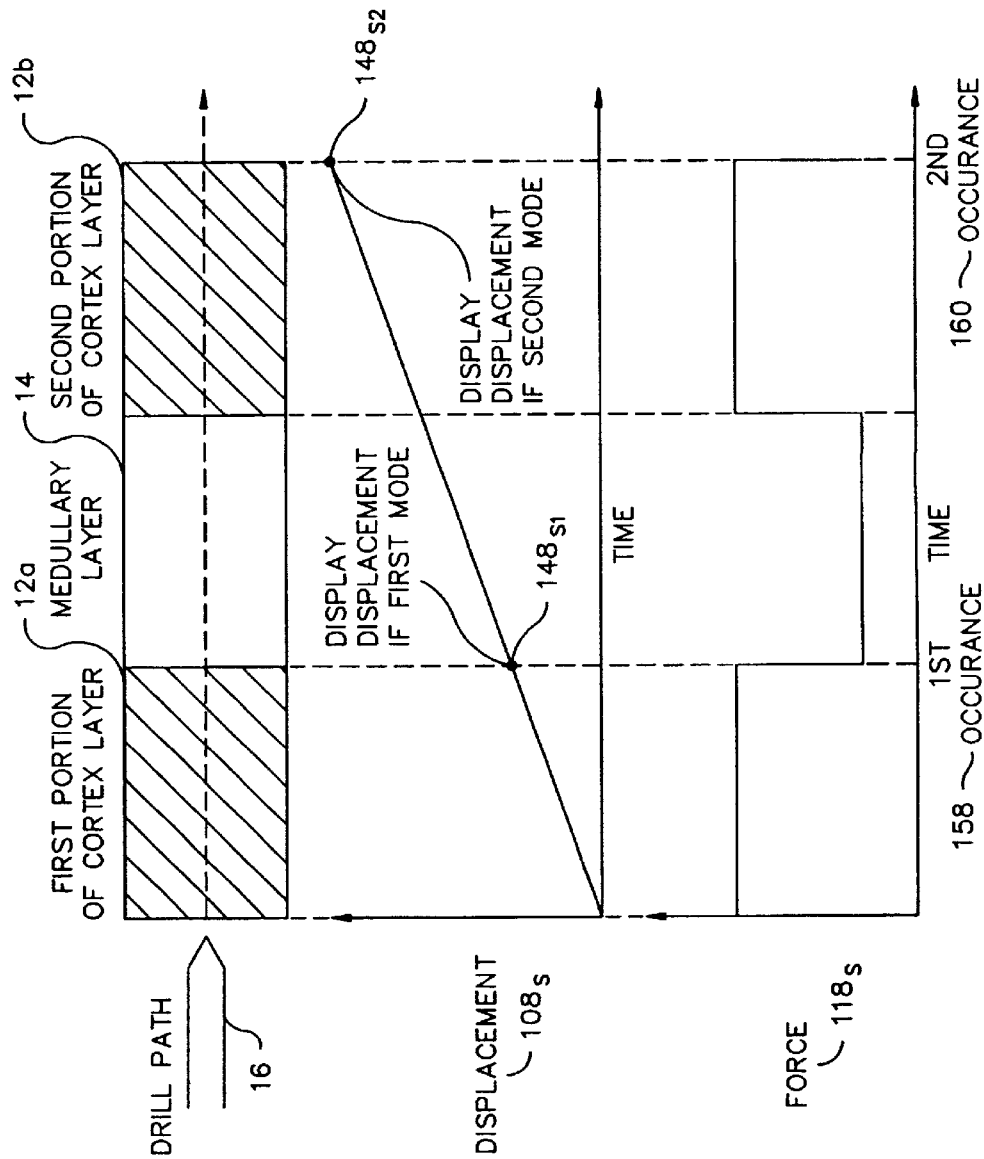
FIGS. 7A, 7B, and 7C are diagrams illustrating the position of the drill bit of FIG. 2 in bicortical bore of FIG. 1B and the corresponding output of the first and second sensors of the displacement and load measurement assemblies of FIG. 2.

Referring to FIGS. 2 and 5–6, the controller assembly 106 is in electrical communication with the first sensor 108 and the second sensor 118. Preferably, the controller assembly 106 has a controller housing 146 integral with the drill housing 26. The controller assembly includes a processor 148 in electrical communication with the first and second sensors 108, 118 and with a mode selector 150 having a mode selector switch 154 and a display 152 having a reset button 153. The display 152, the reset button 154 and the mode selector switch 154 are mounted in a panel 156 of the controller housing 146. Alternatively, the display 152 or the reset button 153 or the mode selector 154 or any combination thereof could be separately housed in a remote control unit (not shown) that communicates with the first and second sensors 108, 118 by a wireless link (not shown). The display 152 is for indicating the measured displacement of the leading edge 16a of the drill bit 16 to the user. The display 152 is controlled by the processor 148. The display 152 may continuously indicate the changing displacement of the leading edge 16a of the drill bit 16 during the drilling of a bore and may also indicate the length of the bore at the when the drill bit 16 passes from one medium to another.

Referring to FIGS. 1, 5–6, 7A, 7B, and 7C, the processor 148 is configured to operate in a first mode for drill bit penetration measurement in unicortical bore drilling. In the first mode the processor 148 is configured to output a third signal $148s_1$ representative of the depth of penetration of the leading edge 16a of the drill bit 16 when the leading edge 16a of the drill bit 16 passes from the first medium to the second medium. The third signal $148s_1$ is based on the first and second signals 108s, 118s. Preferably, the third signal $148s_1$ is output upon a first occurrence 158 of a second time derivative of the first signal 108s being greater than zero and a first time derivative of the second signal 118s being less than zero. In other words a positive acceleration of the drill bit 16 and a concurrent reduction in the force applies to the leading edge 16a of the drill bit 16 trigger the first occurrence 158. At the time of the first occurrence 158, the third signal $148s_1$ corresponds to the length of the unicortical drill path.

Preferably, but not necessarily, the processor 148 is also configured to operate in a second mode for drill bit penetration measurement in bicortical bore drilling and the mode selector 150 and mode selector switch 154 are for selecting between the first and second modes. The second mode of operation is directed to the case where the first medium is the cortical bone 12 surrounded by a second medium, such as the air or tissue surrounding the outer surface of the cortical bone 12, and the first medium encloses a third medium, such as the soft medullary layer 14, having a third density. In the second mode, the processor 148 is configured to output the third signal $148s_2$ in response to a second occurrence 160 of the second time derivative of the first signal 108s being greater than zero and the first time derivative of the second signal 118s being less than zero and corresponds to the length of the bicortical drill path. Accordingly, the third signal $148s_2$ is output after the second time the drill bit 16 accelerates with a concurrent reduction in the force applied to the leading edge 16a of the drill bit 16.

Figure 8:
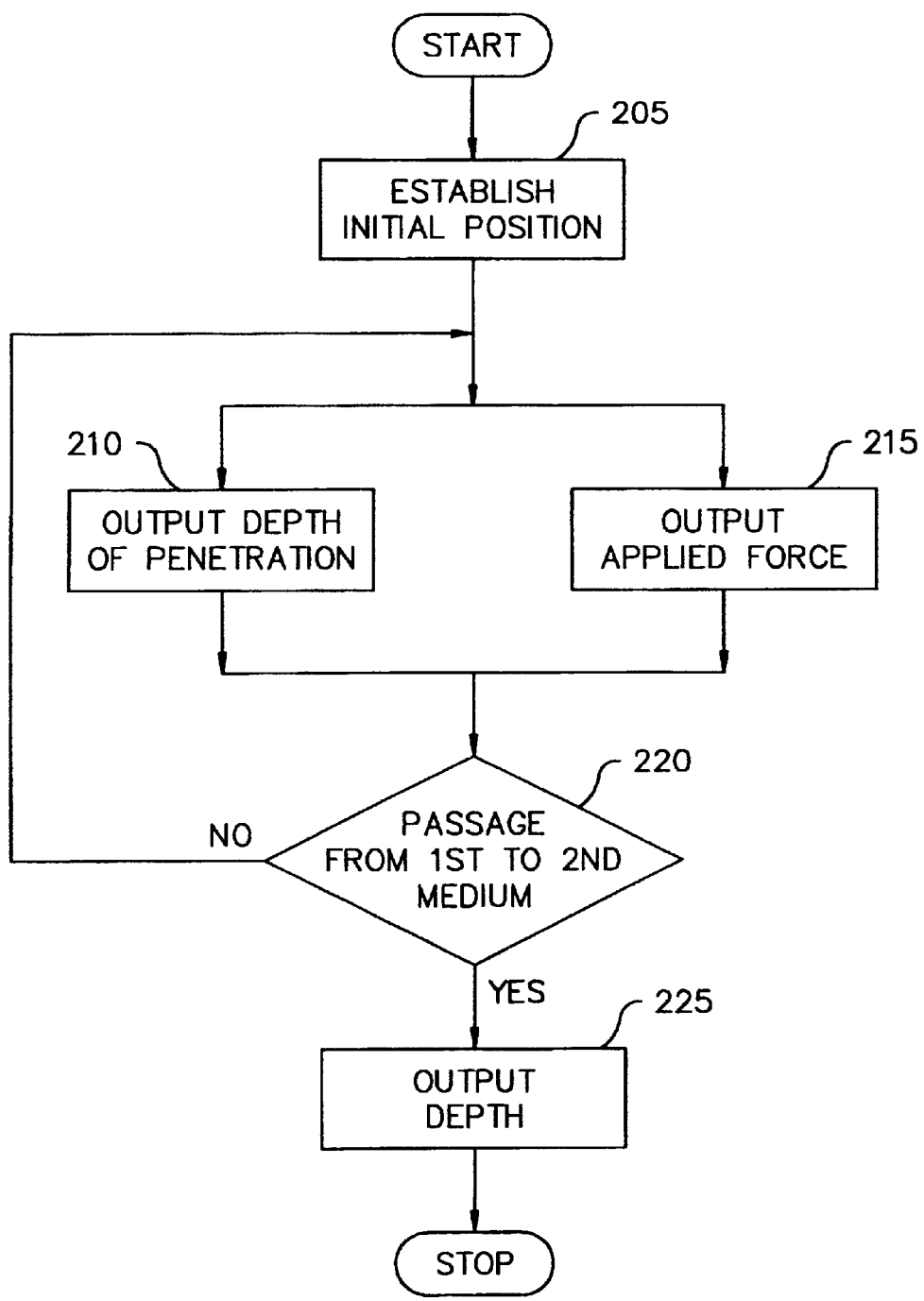
FIG. 8 is a flow diagram of a preferred method for determining the depth of penetration of a drill bit in accordance with the present invention.

Referring to FIG. 8, there is shown a block diagram of a first preferred method for determining, with respect to a reference point, the depth of penetration of the leading edge 16a of a rotating drill bit 16 in a bore when the leading edge 16a of the drill bit 16 transitions from a first medium having a first density, such as the hard outer cortex 12 of a cortical bone 10, to a second adjacent medium having a second density, such air or tissue surrounding the outer surface of the cortical bone 10. (FIG. 1B).

An initial position of the leading edge 16a of the drill bit 16 relative to the reference point is established (Step 205). The initial position preferably is established by placing the leading edge 16a of the drill bit 16 against the outer surface of the cortical bone to be drilled and by extending the distal end 10a of the extension 110 of the displacement measurement assembly 102 to the reference point, such as an anatomical structure proximal to the desired location of the bore to be drilled. With the leading edge 16a of the drill bit 16 and the distal end 110a of the extension 110 in the above positions, the measured displacement of the drill bit 16 is set to zero by pressing the reset button 153. Upon commencement of drilling, a first signal representing the depth of penetration of the leading edge 16a of the rotating drill bit 16 in the bore is output (Step 210). A second signal representing a force applied to the leading edge of the drill bit is output (Step 215). A third signal based on the first and second signals and representative of the depth of penetration of the leading edge of the drill bit when the leading edge of the drill bit passes from the first medium to the second medium is output (Step 220). Preferably, the third signal is output when the second time derivative of the first signal is greater than zero and a first time derivative of the second signal is less than zero.

Figure 9:
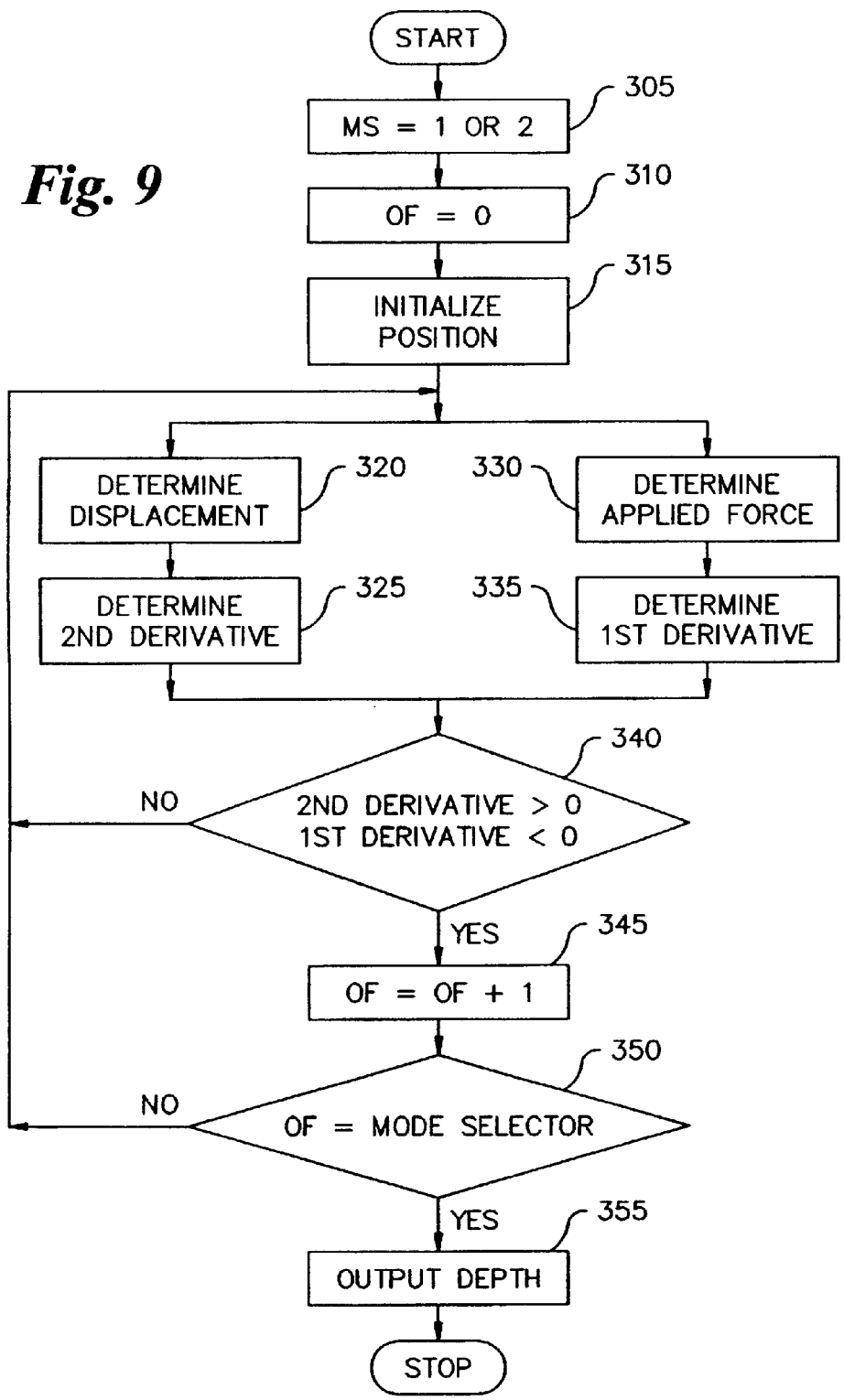
FIG. 9 is a flow diagram of another preferred method for determining the depth of penetration of a drill bit in accordance with the present invention.

Referring to FIG. 9, there is shown a block diagram of a second preferred method for determining, with respect to a reference point, the depth of a drilled unicortical bore 20 or a drilled bicortical bore 18. (FIGS. 1A and 1B). The mode selector switch 15 (MS) is set to the value "1" if a unicortical bore 20 is being drilled or set to the value "2" if a bicortical bore 18 is being drilled (Step 305). An occurrence flag (OF) is set to zero (Step 310). An initial position of the leading edge 16a of the drill bit 16 relative to the reference point is established (Step 315), preferably in a manner similar to Step 205 discussed above. The displacement of the leading edge 16a of the drill bit 16 and the force applied to the leading edge 16a of the drill bit 16 are continuously determined, (Steps 320 and 330, respectively). The second time derivative of the displacement of the leading edge 16a of the drill bit 16 ("drill bit acceleration") is determined (Step 325) and the first time derivative of the force applied to the leading edge 16a of the drill bit 16 ("change in applied force") is determined (Step 335). The occurrence flag is updated by adding one to its present value (Step 345) if the drill bit acceleration is positive and the change in applied force is negative (Step 340), otherwise determination of the displacement and the applied force continues. The depth of the bore is output (Step 355) if the value of the occurrence flag is equal to the value of the mode selector (Step 350), otherwise determination of the displacement and the applied force continues.

The components used to construct the present invention may consist of a variety of materials that are customarily used in the manufacture of surgical drills. One having ordinary skill in the art will readily appreciate the materials that most desirably may be used to construct the present invention. In a preferred embodiment, however, the drilling mechanism, drill bit displacement measurement assembly, the drill bit load measurement assembly and the structural elements of the controller assembly may be constructed of a combination of polymeric materials (e.g., high strength plastic), polymers and stainless steel.

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A drill bit penetration measurement system for determining, with respect to a reference point, a depth of penetration of a leading edge of a rotating drill bit in a bore when the leading edge of the drill bit passes from a first medium to a second medium, the first medium contiguous with the second medium, the first medium having a first density, the second medium having a second density, the system comprising:

a first sensor outputting a first signal representative of a displacement, with respect to the reference point, of the leading edge of the drill bit in the bore;

a second sensor outputting a second signal representative of a force applied to the leading edge of the drill bit;

a processor in electrical communication with the first and second sensors, the processor configured in a first mode to output a third signal representative of the depth of penetration of the leading edge of the drill bit when the leading edge of the drill bit passes from the first medium to the second medium, the third signal based on the first and second signals.

2. The system according to claim 1, wherein the first sensor is a linear variable differential displacement transducer.

3. The system according to claim 1, wherein the second sensor is a load cell.

4. The system according to claim 1, wherein the third signal is output when a second time derivative of the first signal is greater than zero and a first time derivative of the second signal is less than zero.

5. The system according to claim 1, wherein the first sensor is a linear variable differential displacement transducer, the second signal is a load cell, and the third signal is output when the second time derivative of the first signal is greater than zero and a first time derivative of the second signal is less than zero.

6. The system according to claim 1, wherein the first medium is cortical bone surrounded by the second medium and the first medium encloses a third medium having a third density, the system further comprising a mode selector and the processor further configured to operate in a mode selected from the group of modes consisting of:

(a) the first mode wherein the third signal corresponds to a length of a unicortical drill path; and (b) a second mode, wherein the processor is configured such that the third signal corresponds to a length of a bicortical drill path.

7. The system according to claim 6, wherein the first sensor is a linear variable differential displacement transducer;

the second sensor is a load sensor;

the processor, in the first mode, outputs the third signal when a second time derivative of the first signal is greater than zero and a first time derivative of the second signal is less than zero; and the processor, in the second mode, outputs the third signal in response to a second occurrence of the second time derivative of the first signal being greater than zero and the first time derivative of the second signal being less than zero.

8. A drill bit penetration measurement system for determining, with respect to a reference point, a depth of penetration of a leading edge of a rotating drill bit in a bore when the leading edge of the drill bit passes from a first medium to a second medium, the first medium having a first density, the second medium having a second density, the drill bit being rotatably driven by a drive within a drill housing, the system comprising:

a drill bit displacement measurement assembly connected to the drill housing, the displacement measurement assembly having a first sensor outputting a first signal representative of a displacement of the leading edge of the drill bit in the bore;

a drill bit load measurement assembly comprising:
  a housing having an axis of rotation, the housing removably connected to the drive for rotation thereby;
  a thrust assembly about which the housing is rotatable;
  a drill chuck connected to the housing for rotation therewith and to the thrust assembly for rotation with respect thereto, the drill chuck movable in translation along the axis of rotation of the housing; and
  a second sensor connected to the thrust assembly, the second sensor outputting a second signal representative of a force applied to the drill bit; and a controller assembly in electrical communication with the first sensor and the second sensor, the controller assembly having a processor configured in a first mode to output a third signal representative of the depth of penetration of the leading edge of the drill bit when the leading edge of the drill bit passes from the first medium to the second medium, the third signal based on the first and second signals.

9. The system according to claim 8, wherein the thrust assembly is connected to the housing by a first bearing and to the drill chuck by a second bearing.

10. The system according to claim 9, wherein the thrust assembly comprises a tube having a bore therethrough, the bore having a piston movable therein, the piston connected to the second bearing.

11. The system according to claim 10, wherein the second sensor is a pressure transducer and a portion of the bore forms a hydraulic chamber connecting the second sensor with the piston.

12. The system according to claim 10, wherein the second sensor is a piezo-electric device adjacent the piston and a portion of the bore forms a conduit through which passes an electrical conductor connecting the piezo-electric device to the processor.

13. The system according to claim 8, wherein the housing has a slot and the drill chuck has a tab extending into the slot and moveable therein in translation along the axis of rotation of the housing.

14. A method for determining, with respect to a reference point, a depth of penetration of a leading edge of a rotating drill bit in a bore when the leading edge of the drill bit transitions from a first medium to a second medium, the first medium adjacent the second medium, the first medium having a first density, the second medium having a second density, the method comprising:

establishing an initial position of the leading edge of the drill bit with respect to the reference point;

outputting a first signal representing the depth of penetration of the leading edge of the rotating drill bit in the bore;

outputting a second signal representing a force applied to the leading edge of the drill bit;

outputting a third signal representative of the depth of penetration of the leading edge of the drill bit when the leading edge of the drill bit passes from the first medium to the second medium, the third signal based on the first and second signals.

15. The method according to claim 14, further comprising:

determining a second time derivative of the first signal; and determining a first time derivative of the second signal; and and wherein the third signal is output when the second time derivative of the first signal is greater than zero and the first time derivative of the second signal is less than zero.

16. The method claim according to claim 15, wherein the first medium is cortical bone surrounded by the second medium and the first medium encloses a third medium having a third density, and the method further comprises selecting a mode from the group of modes consisting of:

(a) a first mode wherein the third signal corresponds to a length of a unicortical drill path; and (b) a second mode, wherein the processor is configured such that the third signal corresponds to a length of a bicortical drill path.

* * * * *